US010548907B2

(12) United States Patent
Khairatkar-Joshi et al.

(10) Patent No.: US 10,548,907 B2
(45) Date of Patent: *Feb. 4, 2020

(54) TREATMENT OF ALLERGIC RHINITIS USING A COMBINATION OF MOMETASONE AND OLOPATADINE

(71) Applicant: Glenmark Pharmaceuticals Limited, Mumbai (IN)

(72) Inventors: Neelima Khairatkar-Joshi, Thane (IN); Abhay Kulkarni, Navi Mumbai (IN); Dinesh Pradeep Wale, District-Osmanabad (IN); Vikram Mansingh Bhosale, Mumbai (IN); Piyush Agarwal, Mumbai (IN); Patrick Keohane, London (GB); Sudeesh K. Tantry, Jamison, PA (US); Chad Oh, Mahwah, NJ (US)

(73) Assignee: Glenmark Specialty S.A., La-Chaux-de-Fonds (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/682,001

(22) Filed: Apr. 8, 2015

(65) Prior Publication Data

US 2015/0272966 A1    Oct. 1, 2015

Related U.S. Application Data

(63) Continuation-in-part of application No. 14/506,122, filed on Oct. 3, 2014.

(30) Foreign Application Priority Data

Oct. 4, 2013    (IN) .......................... 3174/MUM/2013

(51) Int. Cl.
*A61K 31/58* (2006.01)
*A61K 31/335* (2006.01)
*A61K 9/00* (2006.01)

(52) U.S. Cl.
CPC ............ *A61K 31/58* (2013.01); *A61K 9/0043* (2013.01); *A61K 31/335* (2013.01)

(58) Field of Classification Search
CPC .. A61K 31/355; A61K 31/58; A61K 31/0043; A61K 31/573; A61K 2300/00
See application file for complete search history.

(56) References Cited

U.S. PATENT DOCUMENTS

| 4,871,865 | A | 10/1989 | Lever, Jr. et al. |
| 4,923,892 | A | 5/1990 | Lever, Jr. et al. |
| 5,837,699 | A | 11/1998 | Sequeira et al. |
| 6,127,353 | A | 10/2000 | Yuen et al. |
| 6,841,146 | B2 | 1/2005 | Haslwanter et al. |
| 7,977,376 | B2 | 7/2011 | Singh et al. |
| 8,399,508 | B2 | 3/2013 | Singh et al. |
| 9,078,923 | B2 | 7/2015 | Dhuppad et al. |
| 2004/0097474 | A1 | 5/2004 | Cagle et al. |
| 2006/0110328 | A1 | 5/2006 | Cagle et al. |
| 2008/0058296 | A1 | 3/2008 | Chaudry |
| 2012/0121653 | A1 | 5/2012 | Jenkins et al. |
| 2015/0099725 | A1 | 4/2015 | Khairatkar-Joshi et al. |
| 2015/0250718 | A1 | 9/2015 | Dhuppad et al. |
| 2016/0287612 | A1 | 10/2016 | Dhuppad et al. |

FOREIGN PATENT DOCUMENTS

| EP | 2014305 A1 | 1/2009 |
| WO | WO-1995020393 A1 | 8/1995 |
| WO | WO-0126658 A2 | 4/2001 |
| WO | WO-2006057769 A2 | 6/2006 |
| WO | WO-2009003199 A1 | 12/2008 |
| WO | WO-2010009028 A1 | 1/2010 |
| WO | WO-2010025236 A1 | 3/2010 |
| WO | WO-2011008923 A2 | 1/2011 |
| WO | WO-2011141929 A2 | 11/2011 |
| WO | WO-2012094283 A2 | 7/2012 |
| WO | WO-2014092346 A1 | 6/2014 |

OTHER PUBLICATIONS

Meltzer et al. (J Allergy Clin Immunol, Jul. 1998).*
Maiti et al. (J of Pharmacology and Pharmacotherapeutics, Oct.-Dec. 2011, 2(4), 270-276).*
Okubo et al. (Current Medical Research and Opinion, 2010, 1657-1665).*
Nsouli, et al., Combination of a nasal antihistamine olopatadine and a nasal corticosteroid, mometasone . . . , International Scientific Conference, Dubai, UAE, Dec. 2010.
Austin, et al., Mometasone Furoate is a less specific Glucocorticoid than Fluticasone Propionate, European Respiratory Journal, 2002, 20:1386-1392.
Johnson, M. Ph.D., Development of Fluticasone Propionate and Comparison with other Inhaled Corticosteroids, J. Allergy Clin. Immunol, 1998, 101:4:2:S434-S439.
International Search Report for International Application No. PCT/IB2015/065035 dated Jan. 9, 2015.
Ratner, et al., Ann. Allergy Asthma Immunol, 2005, 95:474-479.
Anolik R., Int Arch Allergy Immunol, 2008, 147:323-330.
Anolik R., Allergy Asthma Proc, 2009, 30:406-412.
Simpson, Ann Allergy, 1994, 73:497-502.
Ratner et al, J Fam Pract. 1998, 47(2):118-25.
Bernstein et al., Respiratory Medicine, 1999, 93:603-612.
Aneeza et al., Allergy Rhinol, 2013, 4:e120-e126.

(Continued)

*Primary Examiner* — Umamaheswari Ramachandran
(74) *Attorney, Agent, or Firm* — Blank Rome LLP (57) ABSTRACT

The present invention relates to a method of treating allergic rhinitis in a subject (e.g., a human) in need thereof comprising nasally administering to the subject an effective amount of a fixed-dose pharmaceutical composition comprising mometasone or its salt and olopatadine or its salt.

32 Claims, 3 Drawing Sheets

(56) References Cited

OTHER PUBLICATIONS

Meltzer et al., J Allergy Clin Immunol, 1999, 104(1):107-114.
Herbert et al., Allergy, 1996, 51:569-576.
Dibildox, J Allergy Clin Immunol, 108(1):S54-S58, 2001.
Navarro et al., J Investig Allergol Clin Rhinitis, 2011, 21(5):363-369.
LaForce et al., Allergy Asthma Proc, 2010, 31:132-140.
Derendorf et al, Eur Respir J, 2001, 17:157-158.
Buck, "Intranasal steroids for children with allergic rhinitis", Pediatric Pharmacology, May 2001, vol. 7, No. 5.
Meltzer et al, Ann Allergy Asthma Immunol, 2005, 95:600-606.
Anolik, et al., Ann Allergy Asthma Immunol., 2008, 100:264-271.
Barnes, et al., Clinical and Experimental Allergy, 2006, 36:676-684.
Benincasa, et al., Drug Invest. 1994, 8(4):225-233.
Di Lorenzo, et al., Clin Exp Allergy, 2004, 34:259-267.
Juniper, et al., J Allergy Clin Immunol, 1989, 83:627-33.
Prescribing information for Patanase® (Feb. 2012).
Prescribing information for Nasonex® (Jan. 2011).
U.S. Appl. No. 14/483,837, filed Sep. 11, 2014.
Bajaj et al., The Internet Journal of Otorhinolaryngology, 2006, vol. 6, No. 1.
Roland, Expert Opin Pharmacother, 2010, 11(9), 1559-1567.
Prenner, et al., Mometasone Furoate Nasal Spray Reduces the Ocular Symptoms of Seasonal Allergic Rhinitis, J Allergy Clin Immunol, Jun. 2010, 1247-1253.
Amrol, et al., Intranasal Steroids for Ocular Symptoms in Allergic Rhinitis, http://www.jwatch.org/jw201006100000003/2010/06/10/intranasal-steroids-ocular-symptoms-allergic.
Bousquet, et al., Onset of Action of the Fixed Combination Intranasal Azelastine-Fluticasone Propionate in an Allergen Exposure Chamber, J Allergy Clin Immunol Pract, 2018, 1-7.e6 (13 pgs).

Supplementary European Search Report issued in EP18823894 dated Apr. 8, 2019.
Glenmark Pharmaceuticals: Glenmark Pharmaceuticals Reports Positive Results from a Phase 3 Trial of GSP 301, Mar. 29, 2017 (Mar. 29, 2017), XP055444412, Retrieved from the Internet: URL:https://www.prnewswire.com/news-releases/glenmark-pharmaceuticals-reports-positive-results-from-a-phase-3-trial-of-gsp-301-mometasoneolopatadine-fixed-dose-combination-nasal-spray-in-seasonal-allergic-rhinitis-300431125.html [retrieved on Jan. 25, 2018] the whole document.
Anonymous: NCT02870205 on May 3, 2017: ClinicalTrials.gov Archive, May 3, 2017 (May 3, 2017), XP055444415, Retrieved from the Internet: URL:https://clinicaltrials.gov/archive/NCT02870205/2017 05 03 [retrieved on—Jan. 25, 2018] the whole document.
Anonymous: NCT02631551 on May 18, 2017: Clinical Trials.gov Archive, May 18, 2017 (May 18, 2017), XP055444418, Retrieved from the Internet: URL:https://clinicaltrials.gov/archive/NCT02631551/2017 05 18 [retrieved on—Jan. 25, 2018].
Kaliner et al: Azelastine and olopatadine in the treatment of allergic rhinitis, Annals of Allergy, Asthma & Immunology, Arlington Heights, IL, US, vol. 103, No. 5, Nov. 1, 2009 (Nov. 1, 2009), pp. 373-380, XP026960456, ISSN: 1081-1206 [retrieved on Nov. 1, 2009] the whole document.
Anonymous: to Study GSP 301 in Patients With Seasonal Allergic Rhinitis—Study Results—ClinicalTrials.gov, Jun. 28, 2017 (Jun. 28, 2017), XP055445229, Retrieved from the Internet: URL:https://www.clinicaltrials.gov/ct2/show/results/NCT02318303?term=NCT02318303&rank=I =X4370156#othr [retrieved on Jan. 26, 2018] the whole document.
International Search Report issued in PCT/IB2019/051465 dated May 21, 2019.

* cited by examiner

TREATMENT OF ALLERGIC RHINITIS USING A COMBINATION OF MOMETASONE AND OLOPATADINE

This patent application is a continuation-in-part of U.S. patent application Ser. No. 14/506,122, filed Oct. 3, 2014, which claims the benefit of Indian Provisional Patent Application number 3174/MUM/2013, filed Oct. 4, 2013, each of which is hereby incorporated by reference in its entirety.

TECHNICAL FIELD OF THE INVENTION

The present patent application relates to a method of treating allergic rhinitis in a subject (preferably a human) by administering a combination of mometasone or its salt and olopatadine or its salt.

BACKGROUND OF THE INVENTION

Allergic rhinitis is a medical term for inflammation and irritation of the mucous membrane inside the nose. It generally occurs when an allergen such as pollen, dust, or animal dander (particles of shed skin and hair) is inhaled by an individual with a sensitized immune system. Allergic rhinitis may cause additional symptoms such as rhinorrhea (excess nasal secretion), sneezing, nasal itching, nasal congestion and obstruction, coughing, headache, fatigue and malaise. Symptoms may vary in severity between individuals.

Many treatment options are available for treating allergic rhinitis such as, for example, antihistamines (e.g., cetirizine and loratadine), steroids (e.g., triamcinolone), decongestants, and leukotriene receptor antagonists (e.g., montelukast). These treatments are generally administered orally or nasally and some are associated with unpleasant taste and smell (e.g., Dymista nasal spray, which is a combination of azelastine and fluticasone propionate).

Olopatadine hydrochloride, an antihistamine, is chemically described as (Z)-11-[3-(dimethylamino)propylidene]-6,11-dihydrodibenz[b,e]oxepin-2-acetic acid hydrochloride, and is disclosed in U.S. Pat. Nos. 4,871,865 and 4,923,892. It is commercially available in the United States as PATANASE® Nasal Spray, which contains 0.6% w/v olopatadine (base) in a non-sterile aqueous solution. It is indicated for the relief of the symptoms of seasonal allergic rhinitis (SAR) in adults and children 6 years of age and older.

Mometasone furoate is a glucocorticosteroid used topically to reduce inflammation of the skin or in the airways. Mometasone furoate monohydrate is commercially available in the United States as NASONEX®, a nasal spray indicated for (i) the treatment of nasal symptoms of allergic rhinitis in patients ≥2 years of age, (ii) the treatment of nasal congestion associated with seasonal allergic rhinitis in patients ≥2 years of age, (iii) the prophylaxis of seasonal allergic rhinitis in patients ≥12 years of age, and (iv) the treatment of nasal polyps in patients ≥18 years of age. It is available as 50 mcg in a metered-dose, manual pump spray unit containing an aqueous suspension of mometasone furoate monohydrate equivalent to 0.05% w/w mometasone furoate (calculated on the anhydrous basis).

International Publication No. WO 2011/141929 discloses an aqueous nasal spray solution comprising fluticasone and olopatadine.

U.S. Pat. No. 6,127,353 discloses a pharmaceutical composition of mometasone furoate monohydrate.

U.S. Pat. Nos. 7,977,376 and 8,399,508 disclose a topical formulation of olopatadine hydrochloride.

International Publication No. WO 2011/008923 discloses a nasal spray regimen of olopatadine for children.

International Publication No. WO 1995/020393 discloses the use of mometasone furoate for treating airway passage and lung diseases.

International Publication No. WO 2010/025236 discloses a combination of a nasal steroid and a nasal antihistamine for the treatment of viral upper respiratory tract infections, upper respiratory infections, and common colds.

There still exists a need for easy to use and effective treatments for allergic rhinitis.

SUMMARY OF THE INVENTION

The present invention relates to a fixed dose combination of mometasone or its salt and olopatadine or its salt and its use for the treatment of rhinitis in a subject in need thereof. The inventors have surprisingly found that mometasone furoate and olopatadine hydrochloride act synergistically in the treatment of allergic rhinitis and the combination is more effective and provides better therapeutic value than treatment with either active ingredient alone.

In an embodiment, the present invention relates to a method of treating allergic rhinitis in a subject (e.g., a human) in need thereof comprising nasally administering to the subject an effective amount of a fixed-dose pharmaceutical composition comprising mometasone or its salt and olopatadine or its salt. Preferably, the composition is nasally administered as 1 or 2 sprays per nostril of the subject at least once daily. Each spray preferably comprises mometasone or its salt and olopatadine or its salt in a weight ratio of about 1:5 to about 1:60, such as in a weight ratio of from about 1:12 to about 1:53, from about 1:13.3 to about 1:50, or from about 1:18 to about 1:40 (based on the equivalent weight of olopatadine free base). In one embodiment, the fixed-dose pharmaceutical composition is a suspension wherein the mometasone or its salt is present in particulate form and the olopatadine or its salt is present in dissolved form.

In another embodiment, the present invention relates to a method of treating allergic rhinitis in a subject (e.g., a human) in need thereof comprising nasally administering to the subject an effective amount of a fixed-dose pharmaceutical composition comprising mometasone furoate monohydrate and olopatadine hydrochloride. In one preferred embodiment, the composition is nasally administered as 1 or 2 sprays per nostril of the subject at least once daily. Each spray of the pharmaceutical composition may comprise olopatadine hydrochloride equivalent to about 300 mcg, about 450 mcg, about 600 mcg, about 750 mcg, or about 900 mcg of olopatadine, and about 12.5 mcg, about 25 mcg, about 37.5 mcg, about 50 mcg, or about 62.5 mcg of mometasone furoate. In one embodiment, each spray comprises olopatadine hydrochloride equivalent to about 600 mcg of olopatadine and about 25 mcg of mometasone furoate. In another embodiment, each spray comprises olopatadine hydrochloride equivalent to about 600 mcg of olopatadine and about 50 mcg of mometasone furoate.

Allergic rhinitis in the context of present invention includes, but is not limited to, inflammation and irritation of the mucous membrane inside the nose, and nasal and/or non-nasal symptoms associated therewith. It includes, for example, persistent allergic rhinitis, perennial allergic rhinitis, seasonal allergic rhinitis, chronic rhinitis, rhinitis medicamentosa, vasomotor rhinitis, infective rhinitis, autonomic rhinitis, hormonal rhinitis, drug-induced rhinitis, atrophic rhinitis, and gustatory rhinitis. Preferably, the allergic rhinitis is selected from perennial allergic rhinitis, persistent allergic rhinitis, seasonal allergic rhinitis, and nasal and/or non-nasal symptoms associated therewith.

In the context of the present invention, symptoms associated with rhinitis includes rhinorrhea, nasal congestion, nasal itching, sneezing, itching/burning eyes, tearing/watering eyes, redness of eyes, itching of ears or palate, coughing, ocular pruritus, excess lacrimation, headache, fatigue and malaise.

In another embodiment, of the present invention relates to a method of treating allergic rhinitis in a subject (e.g., a human) in need thereof, the method comprising nasally administering to the subject an effective amount of a fixed-dose pharmaceutical composition comprising mometasone or its salt and olopatadine or its salt in a weight ratio of about 1:5 to about 1:60 or from about 1:12 to about 1:53, wherein (i) the composition is nasally administered as 1 or 2 sprays per nostril, once or twice daily, and (ii) each spray comprises olopatadine hydrochloride equivalent to about 600 mcg of olopatadine and about 25 mcg to about 50 mcg of mometasone furoate. In one embodiment, the composition is administered for about 1 week. In another aspect of the embodiment, the composition is administered for about 2 weeks.

In one embodiment, the total nasal symptoms score (TNSS) of the human subject is reduced by at least 40%, preferably by at least 50% from baseline after 1 or 2 weeks treatment. In another embodiment, the total ocular symptom score (TOSS) of the human subject is reduced by at least 30%, preferably by at least 40% from baseline after 1 or 2 weeks treatment. In an aspect of the invention, the total nasal symptoms score (TNSS) and the total ocular symptom score (TOSS) can be observed as instantaneous or reflective or both.

In one embodiment, the subject suffers from persistent allergic rhinitis and is treated for 4 or 6 weeks.

In another embodiment, the subject exhibits a positive skin prick test to an allergen. Alternately, the subject may also exhibit positive blood tests showing an allergy.

In yet another embodiment, the method involves no significant treatment-related adverse effects in the subject after 1 or 2 weeks treatment.

In another embodiment, the present invention relates to a method of treating seasonal allergic rhinitis and/or nasal symptoms associated with seasonal allergic rhinitis in a subject (e.g., a human) in need thereof comprising nasally administering to the subject a combination (e.g., synergistic combination) comprising mometasone furoate and olopatadine hydrochloride, wherein the combination is in the form of a pharmaceutical composition comprising mometasone furoate and olopatadine hydrochloride in a weight ratio of about 1:5 to about 1:60 or from about 1:13.3 to about 1:53.2 (based on the equivalent weight of olopatadine free base). In one embodiment, the present invention relates to a method of treating allergic rhinitis in a human in need thereof comprising nasally administering to the human an effective amount of a fixed-dose pharmaceutical composition comprising mometasone or its salt and olopatadine or its salt, wherein (i) the composition is nasally administered as 1 or 2 sprays per nostril of the human at least once daily, and (ii) each spray comprises mometasone or its salt and olopatadine or its salt in a weight ratio of about 1:5 to about 1:60 or from about 1:13.3 to about 1:53.2 (based on the equivalent weight of olopatadine free base). The method may provide reduction in at least one treatment-related adverse effect (e.g. epistaxis and somnolence) relative to the use of the mometasone or olopatadine alone. For example, the method may provide effective treatment of seasonal allergic rhinitis and/or nasal symptoms associated with seasonal allergic rhinitis in a subject with a reduced incidence of drowsiness and nose bleeds. In another embodiment, the method may provide effective treatment of seasonal allergic rhinitis and/or nasal symptoms associated with seasonal allergic rhinitis in a subject without significant drowsiness and/or inducing nose bleeds.

In another embodiment, the present invention relates to a method of treating perennial allergic rhinitis and/or nasal symptoms associated with perennial allergic rhinitis in a subject (e.g., a human) in need thereof comprising nasally administering to the subject a combination (e.g., synergistic combination) comprising mometasone furoate and olopatadine hydrochloride, wherein the combination is in the form of a pharmaceutical composition comprising mometasone furoate and olopatadine hydrochloride in a weight ratio of about 1:5 to about 1:60 or from about 1:13.3 to about 1:53.2 (based on the equivalent weight of olopatadine free base).

In one aspect of this embodiment, each spray comprises about 25 mcg or about 50 mcg mometasone furoate and olopatadine hydrochloride equivalent to about 600 mcg olopatadine. In one aspect of this embodiment, the pharmaceutical composition is a suspension comprising mometasone or its salt in particulate form and olopatadine or its salt in solution. In one aspect of this embodiment, the composition is administered for a period of at least 1 week as—(i) 1 spray per nostril once daily or twice daily, or (ii) 2 sprays per nostril once daily or twice daily. In yet another aspect of this embodiment, the allergic rhinitis is selected from perennial allergic rhinitis, persistent allergic rhinitis, seasonal allergic rhinitis, and nasal and/or non-nasal symptoms associated therewith. In a preferred aspect, the allergic rhinitis is seasonal allergic rhinitis and/or nasal symptoms associated therewith. In yet another aspect of this embodiment, (i) the total nasal symptoms score (TNSS) of the human is reduced by at least 50% from baseline after 2 weeks treatment, and/or (ii) total ocular symptom score (TOSS) of the human is reduced by at least 40% from baseline after 2 weeks treatment, and/or (iii) no significant treatment-related adverse effects are observed in the human after 2 weeks treatment. In one aspect of the said embodiment, the human exhibits a positive skin prick test to an allergen. In one embodiment, the treatment-related adverse effects include somnolence or epistaxis or a combination thereof.

The fixed-dose pharmaceutical composition comprising mometasone or its salt and olopatadine or its salt may be administered to the subject according to one of the following regimens:
  a) the composition is nasally administered as 1 spray per nostril once daily for a period of at least 1 week;
  b) the composition is nasally administered as 2 sprays per nostril once daily for a period of at least 1 week;
  c) the composition is nasally administered as 1 spray per nostril twice daily for a period of at least 1 week;
  d) the composition is nasally administered as 2 sprays per nostril twice daily for a period of at least 1 week;
  e) the composition is nasally administered as 1 spray per nostril once daily for a period of 2 weeks;
  f) the composition is nasally administered as 2 sprays per nostril once daily for a period of 2 weeks;
  g) the composition is nasally administered as 1 spray per nostril twice daily for a period of 2 weeks; or
  h) the composition is nasally administered as 2 sprays per nostril twice daily for a period of 2 weeks.

In another embodiment, the present invention relates to a method of treating seasonal allergic rhinitis and/or nasal symptoms associated with seasonal allergic rhinitis in a human in need thereof comprising nasally administering to the human a combination (e.g., synergistic combination) comprising mometasone furoate and olopatadine hydrochloride, wherein the combination is in the form of a pharmaceutical composition comprising mometasone furoate in particulate form and olopatadine hydrochloride in solution in a weight ratio of about 1:13.3 to about 1:53.2 (based on the equivalent weight of olopatadine free base), and wherein the composition is administered as 1 or 2 sprays per nostril of the human, at least once daily for a period of at least 1 week wherein the method provides reduction of at least one treatment-related adverse effect.

In one aspect of this embodiment, the composition is administered once daily or twice daily for a period of 2 weeks. In another aspect of this embodiment, each spray comprises about 25 mcg or about 50 mcg of mometasone furoate and about 665 mcg of olopatadine hydrochloride. In yet another aspect of this embodiment, (i) the total nasal symptoms score (TNSS) of the human is reduced by at least 50% from baseline after 2 weeks treatment, and/or (ii) total ocular symptom score (TOSS) of the human is reduced by at least 40% from baseline after 2 weeks treatment, and/or (iii) no significant treatment-related adverse effects are observed in the human after 2 weeks treatment. In one aspect of the said embodiment, the human exhibits a positive skin prick test to an allergen. Preferably, the treatment-related adverse effects include somnolence or epistaxis or a combination thereof.

In an aspect of the invention, the fixed-dose pharmaceutical composition may be administered for a period of about 1 week, 2 weeks, 4 weeks, 6 weeks or 8 weeks. Preferably, the fixed-dose pharmaceutical composition, is administered as 1 or 2 sprays per nostril of the subject (e.g., a human), once daily or twice daily for a period of 1 week or 2 weeks. In another aspect of the embodiment, each spray of the composition comprises olopatadine hydrochloride equivalent to about 600 mcg of olopatadine and about 25 mcg to about 50 mcg of mometasone furoate. Preferably, each spray of the composition comprises about 665 mcg of olopatadine hydrochloride (equivalent to about 600 mcg of olopatadine) and about 25 mcg or about 50 mcg of mometasone furoate. In yet another aspect, the composition does not have unpleasant odor and taste. In yet another aspect of the embodiment, the total nasal symptoms score (TNSS) of the human subject is reduced by at least 40% or at least 50% from baseline after 1 or 2 weeks treatment. In yet another aspect of the embodiment, the total ocular symptom score (TOSS) of the human is reduced by at least 30% or at least 40% from baseline after 1 or 2 weeks treatment. In yet another aspect of the embodiment, the said method provides reduction in one or more treatment-related adverse effects. Preferably, the treatment-related adverse effects include somnolence or epistaxis or a combination thereof. In yet another aspect of the embodiment, the human subject is a patient exhibiting a positive skin prick test to an allergen.

In one aspect the present invention relates to the use of mometasone or its salt and olopatadine or its salt in a weight ratio of about 1:5 to about 1:60 or from about 1:12 to about 1:53 for the manufacture of a fixed-dose pharmaceutical composition of the invention for the treatment of allergic rhinitis in a subject (e.g., a human) in need thereof. In an aspect, the fixed-dose pharmaceutical composition is a suspension wherein mometasone or its salt is present in particle form (e.g., having a mean particle size of from about 1 to about 20 μm, or from about 1 to about 15 μm) and olopatadine or its salt is present in dissolved form. In yet another aspect the composition does not have unpleasant odor and taste.

In a separate embodiment the present invention relates to a method of reducing symptoms associated with rhinitis in a subject (e.g. a human) in need thereof, the method comprising nasally administering to the subject an effective amount of a fixed dose pharmaceutical composition comprising mometasone or its salt and olopatadine or its salt in a weight ratio of about 1:5 to about 1:60 or from about 1:12 to about 1:53 for about 1 or 2 weeks.

In yet another embodiment, the present invention relates to a method of reducing symptoms associated with allergic rhinitis in a human in need thereof comprising nasally administering to the human an effective amount of a fixed-dose pharmaceutical composition comprising mometasone or its salt and olopatadine or its salt, wherein (i) the composition is nasally administered as 1 or 2 sprays per nostril of the human at least once daily, and (ii) each spray comprises mometasone or its salt and olopatadine or its salt in a weight ratio of about 1:5 to about 1:60 or from about 1:12 to about 1:53 for about 1 or 2 weeks (based on the equivalent weight of olopatadine free base) and wherein the composition is administered as 1 or 2 sprays per nostril of the human, at least once daily for a period of at least 1 week, wherein the method provides reduction of at least one treatment-related adverse effect. In one aspect of this embodiment, each spray comprises about 25 mcg or about 50 mcg mometasone furoate and olopatadine hydrochloride equivalent to about 600 mcg olopatadine. In one aspect of this embodiment, the pharmaceutical composition is a suspension comprising mometasone or its salt in particulate form and olopatadine or its salt in solution. In one aspect of this embodiment, the composition is administered for a period of at least 1 week as—(i) 1 spray per nostril once daily or twice daily, or (ii) 2 sprays per nostril once daily or twice daily. In yet another aspect of this embodiment, the allergic rhinitis is selected from perennial allergic rhinitis, persistent allergic rhinitis, seasonal allergic rhinitis, and nasal and/or non-nasal symptoms associated therewith. In a preferred aspect, the allergic rhinitis is seasonal allergic rhinitis and/or nasal symptoms associated therewith. In yet another aspect of this embodiment, (i) the total nasal symptoms score (TNSS) of the human is reduced by at least 50% from baseline after 2 weeks treatment, and/or (ii) total ocular symptom score (TOSS) of the human is reduced by at least 40% from baseline after 2 weeks treatment, and/or (iii) no significant treatment-related adverse effects are observed in the human after 2 weeks treatment. In one aspect of the said embodiment, the human exhibits a positive skin prick test to an allergen. In one aspect of the said embodiment, the symptoms includes rhinorrhea, nasal congestion, nasal itching, sneezing, itching/burning eyes, tearing/watering eyes, redness of eyes, itching of ears or palate, coughing, ocular pruritus, excess lacrimation, headache, fatigue and malaise. In yet another aspect of the embodiment, the treatment-related adverse effects include somnolence or epistaxis or a combination thereof.

Another embodiment relates to a method of reducing eosinophil count in the nasal lavage of a subject by nasally administering an effective amount of a fixed-dose pharmaceutical composition comprising mometasone or its salt and olopatadine or its salt in a weight ratio of about 1:5 to about 1:60 (based on the equivalent weight of olopatadine free base), wherein the method provides a greater reduction in eosinophil count than that provided by mometasone or its salt or olopatadine or its salt when administered as a monotherapy. The eosinophil count can be measured by any known technique, such as with a hemocytometer.

Yet another embodiment relates to a method of reducing total cell count in the nasal lavage by nasally administering an effective amount of a fixed-dose pharmaceutical composition comprising mometasone or its salt and olopatadine or its salt in a weight ratio of about 1:5 to about 1:60 (based on the equivalent weight of olopatadine free base) wherein the method provides a greater reduction in total cell count than that provided by mometasone or its salt or olopatadine or its salt when administered as a monotherapy.

DETAILED DESCRIPTION OF THE INVENTION

Definitions

The terms used herein are defined as follows. If a definition set forth in the present application and a definition set forth earlier in a provisional application from which the present applications claims priority are in conflict, the definition in the present application shall control the meaning of the terms.

The term "effective amount" or "therapeutically effective amount" denotes an amount of an active ingredient that, when administered to a subject for treating allergic rhinitis, produces an intended therapeutic benefit in a subject. The term "active ingredient" (used interchangeably with "active" or "active substance" or "drug") as used herein includes mometasone or its salt and olopatadine or its salt.

By "salt" or "pharmaceutically acceptable salt", it is meant those salts which are, within the scope of sound medical judgment, suitable for use in contact with the tissues of humans and lower animals without undue toxicity, irritation, and allergic response, commensurate with a reasonable benefit to risk ratio, and effective for their intended use. Representative acid additions salts include, but are not limited to, hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, furoate, succinate, tartrate, ascorbate, glucoheptonate, lactobionate, and lauryl sulphate salts. Representative alkali or alkaline earth metal salts include, but are not limited to, sodium, calcium, potassium and magnesium salts. Preferably, the mometasone salt is mometasone furoate (e.g., mometasone furoate monohydrate) and the olopatadine salt is olopatadine hydrochloride.

As used herein, the term "mometasone and its salt" also includes hydrates of mometasone and its salts, such as a monohydrate, for example mometasone furoate monohydrate.

All references to the weight of, or a weight ratio including, "olopatadine or its salt" or "olopatadine or its salts" are based on the equivalent weight of olopatadine free base, unless otherwise specified.

The term "treating" or "treatment" as used herein also covers the prophylaxis, mitigation, prevention, amelioration, or suppression of a disorder.

The term "synergistic" or "synergy" as used herein refers to a combination exhibiting an effect greater than would be expected from the sum of the effects of the individual components of the combination alone. The term "synergistic" or "synergy" with regard to the combination of mometasone or its salt with olopatadine or its salt which is used in the treatment allergic rhinitis (for example, in the form of a pharmaceutical composition, a combination product or a kit according to the invention) refers to an efficacy for the treatment of the allergic rhinitis that is greater than would be expected from the sum of their individuals effects. The advantages for the synergistic combinations of the present invention include, but are not limited to, exhibiting enhanced efficacy compared to each of the ingredients when used alone, lowering the required dose of one or more of the active ingredients of the combination, reducing the side effects of one or more of the active compounds of the combination and/or rendering one or more of the active ingredients more tolerable to the subject in need of treatment of the allergic rhinitis.

By "pharmaceutically acceptable excipients", it is meant any of the components of a pharmaceutical composition other than the actives and which are approved by regulatory authorities or are generally regarded as safe for human or animal use.

The term "subject" includes mammals like humans and other animals, such as domestic animals (e.g., household pets including cats and dogs) and non-domestic animals (such as wildlife). Preferably, the subject is a human. The human patient can be of any age. In one embodiment, the human subject is at least 2 years of age, at least 12 years of age, or at least 18 years of age. In another embodiment, the human subject is 18 to 65 years of age.

The term "allergic rhinitis" as used herein refers to an allergic and/or inflammatory disease of nasal mucosa, and includes, but is not limited to, inflammation and irritation of the mucous membrane inside the nose, and nasal and/or non-nasal symptoms associated therewith. Typically the allergic rhinitis includes persistent allergic rhinitis, perennial allergic rhinitis, seasonal allergic rhinitis, chronic rhinitis, rhinitis medicamentosa, vasomotor rhinitis, infective rhinitis, autonomic rhinitis, hormonal rhinitis, drug-induced rhinitis, atrophic rhinitis, and gustatory rhinitis. Preferably, the allergic rhinitis includes perennial allergic rhinitis, persistent allergic rhinitis, seasonal allergic rhinitis, and nasal and/or non-nasal symptoms associated therewith. More preferably, the allergic rhinitis includes seasonal allergic rhinitis, and nasal and/or non-nasal symptoms associated therewith.

In the context of present invention, the nasal and/or non-nasal symptoms associated with allergic rhinitis include, for example, sneezing, nasal itching, rhinorrhea (runny nose or excess nasal secretion), nasal congestion, coughing, ocular pruritus, excess lacrimation, headache, fatigue, and malaise.

Methods of Treatment

The present invention relates to use of a fixed dose combination of mometasone or its salt and olopatadine or its salt for the treatment of allergic rhinitis in a subject in need thereof. The inventors have surprisingly found that mometasone furoate and olopatadine hydrochloride act synergistically in the treatment of allergic rhinitis and their combination is more effective and provides better therapeutic value than treatment with either active ingredient alone.

In an embodiment, the present invention relates to a method of treating allergic rhinitis in a subject (e.g., a human) in need thereof comprising nasally administering to the subject, an effective amount of a fixed-dose pharmaceutical composition comprising mometasone or its salt and olopatadine or its salt. Preferably, the composition is nasally administered as 1 or 2 sprays per nostril of the subject at least once daily. Each spray may comprise mometasone or its salt and olopatadine or its salt in a weight ratio of about 1:5 to about 1:60, from about 1:10 to about 1:55 or from about 1:12 to about 1:53 or from about 1:13.3 to about 1:50. Preferably, the weight ratio of mometasone or its salt to olopatadine or its salt ranges from about 1:18 to about 1:40 or from about 1:24 to about 1:26.6. In an embodiment, the fixed-dose pharmaceutical composition is a suspension wherein mometasone or its salt is present in particulate form and the olopatadine or its salt is present in dissolved form.

Another embodiment relates to a method of treating allergic rhinitis in a subject (e.g., a human) in need thereof comprising nasally administering to the subject an effective amount of a fixed-dose pharmaceutical composition comprising mometasone furoate monohydrate and olopatadine hydrochloride. The composition may be nasally administered as 1 or 2 sprays per nostril of the subject at least once daily. Each spray of the pharmaceutical composition may comprise olopatadine hydrochloride equivalent to about 300 mcg, about 450 mcg, about 600 mcg, about 750 mcg, or about 900 mcg of olopatadine, and about 12.5 mcg, about 25 mcg, about 37.5 mcg, about 50 mcg, or about 62.5 mcg of mometasone furoate. In one embodiment, each spray comprises olopatadine hydrochloride equivalent to about 600 mcg of olopatadine and about 25 mcg of mometasone furoate. In another embodiment, each spray comprises olopatadine hydrochloride equivalent to about 600 mcg of olopatadine and about 50 mcg of mometasone furoate. Preferably, each spray comprises about 665 mcg of olopatadine hydrochloride (equivalent to about 600 mcg of olopatadine) and about 25 mcg or about 50 mcg of mometasone furoate.

Allergic rhinitis in the context of present invention includes, but is not limited to, inflammation and irritation of the mucous membrane inside the nose, and nasal and/or non-nasal symptoms associated therewith. It includes, for example, persistent allergic rhinitis, perennial allergic rhinitis, seasonal allergic rhinitis, chronic rhinitis, rhinitis medicamentosa, vasomotor rhinitis, infective rhinitis, autonomic rhinitis, hormonal rhinitis, drug-induced rhinitis, atrophic rhinitis, and gustatory rhinitis. Preferably, the allergic rhinitis is selected from perennial allergic rhinitis, persistent allergic rhinitis, seasonal allergic rhinitis, and nasal and/or non-nasal symptoms associated therewith.

In the context of the present invention, symptoms associated with rhinitis includes rhinorrhea, nasal congestion, nasal itching, sneezing, itching/burning eyes, tearing/watering eyes, redness of eyes, itching of ears or palate, coughing, ocular pruritus, excess lacrimation, headache, fatigue and malaise.

In another embodiment, the present invention relates to a method of treating allergic rhinitis in a subject in need thereof comprising nasally administering to the human, a fixed-dose pharmaceutical composition comprising mometasone or its salt and olopatadine or its salt in a weight ratio of about 1:5 to about 1:60 or from about 1:12 to about 1:53 or from about 1:13.3 to about 1:50, or from about 1:18 to about 1:40, wherein the composition is nasally administered as 1 or 2 sprays per nostril, once or twice daily. Each spray may comprise olopatadine hydrochloride equivalent to about 600 mcg of olopatadine and about 25 mcg to about 50 mcg of mometasone furoate. In an aspect of the embodiment, the composition is administered for about 1 week. In another aspect of the embodiment, the composition is administered for about 2 weeks.

In one embodiment, the total nasal symptoms score (TNSS) of the human subject is reduced by at least 40%, preferably by at least 50% from baseline after 1 or 2 weeks treatment. In another embodiment, the total ocular symptom score (TOSS) of the human subject is reduced by at least 30%, preferably by at least 40% from baseline after 1 or 2 weeks treatment. In an aspect of the invention, the total nasal symptoms score (TNSS) and the total ocular symptom score (TOSS) can be observed as instantaneous or reflective or both.

In the context of present invention, evaluation of total nasal symptoms scores (TNSS) include the sum of scores of nasal congestion, rhinorrhea, itching and sneezing from baseline to the end of treatment (e.g., 1 or 2 weeks). Further evaluation of the total ocular symptoms scores (TOSS) includes ocular itching, tearing/watery eyes and ocular redness from baseline to the end of treatment.

In one embodiment, the subject suffers from persistent allergic rhinitis and is treated for 4 or 6 weeks.

In another embodiment, the subject exhibits a positive skin prick test to an allergen. Alternately, the subject may also exhibit positive blood tests showing an allergy.

In yet another embodiment, the method involves no significant treatment-related adverse effects in the subject after 1 or 2 weeks treatment.

In another embodiment the present invention relates to a method of treating seasonal allergic rhinitis and/or nasal symptoms associated with seasonal allergic rhinitis in a subject (e.g., a human) in need thereof comprising nasally administering to the subject a synergistic combination comprising mometasone furoate and olopatadine hydrochloride, wherein the combination is in the form of a pharmaceutical composition comprising mometasone furoate and olopatadine hydrochloride in a weight ratio of about 1:5 to about 1:60 or from about 1:13.3 to about 1:53.2 (based on the equivalent weight of olopatadine free base).

In one embodiment, the present invention related to a method of treating allergic rhinitis in a human in need thereof comprising nasally administering to the human an effective amount of a fixed-dose pharmaceutical composition comprising mometasone or its salt and olopatadine or its salt, wherein (i) the composition is nasally administered as 1 or 2 sprays per nostril of the human at least once daily, and (ii) each spray comprises mometasone or its salt and olopatadine or its salt in a weight ratio of about 1:5 to about 1:60 or from about 1:13.3 to about 1:53.2 (based on the equivalent weight of olopatadine free base). The method may provide reduction of at least one treatment-related adverse effect (e.g. epistaxis and somnolence) relative to the use of the mometasone or olopatadine alone. For example, the method may provide effective treatment of seasonal allergic rhinitis and/or nasal symptoms associated with seasonal allergic rhinitis in a subject with a reduced incidence of drowsiness and nose bleeds. In another embodiment, the method may provide effective treatment of seasonal allergic rhinitis and/or nasal symptoms associated with seasonal allergic rhinitis in a subject without significant drowsiness and/or inducing nose bleeds.

In another embodiment, the present invention relates to a method of treating perennial allergic rhinitis and/or nasal symptoms associated with perennial allergic rhinitis in a subject (e.g., a human) in need thereof comprising nasally administering to the subject a combination (e.g., a synergistic combination) comprising mometasone furoate and olopatadine hydrochloride, wherein the combination is in the form of a pharmaceutical composition comprising mometasone furoate and olopatadine hydrochloride in a weight ratio of about 1:5 to about 1:60 or from about 1:13.3 to about 1:53.2 (based on the equivalent weight of olopatadine free base).

In one aspect of this embodiment, each spray comprises about 25 mcg or about 50 mcg mometasone furoate and olopatadine hydrochloride equivalent to about 600 mcg olopatadine. In one aspect of this embodiment, the pharmaceutical composition is a suspension comprising mometasone or its salt in particulate form and olopatadine or its salt in solution. In one aspect of this embodiment, the composition is administered for a period of at least 1 week as—(i) 1 spray per nostril once daily or twice daily, or (ii) 2 sprays per nostril once daily or twice daily. In yet another aspect of this embodiment, the allergic rhinitis is selected from perennial allergic rhinitis, persistent allergic rhinitis, seasonal allergic rhinitis, and nasal and/or non-nasal symptoms associated therewith. In a preferred aspect, the allergic rhinitis is seasonal allergic rhinitis and/or nasal symptoms associated therewith. In yet another aspect of this embodiment, (i) the total nasal symptoms score (TNSS) of the human is reduced by at least 50% from baseline after 2 weeks treatment, and/or (ii) total ocular symptom score (TOSS) of the human is reduced by at least 40% from baseline after 2 weeks treatment, and/or (iii) no significant treatment-related adverse effects are observed in the human after 2 weeks treatment. In one aspect of the said embodiment, the human exhibits a positive skin prick test to an allergen. In one aspect of the said embodiment, the treatment-related adverse effects include somnolence or epistaxis or a combination thereof.

Another embodiment is a method of treating allergic rhinitis in a subject, wherein the subject exhibits a positive skin prick test to an allergen. The skin prick test can be performed by pricking the skin with a needle or pin containing a small amount of ragweed allergen. In one embodiment, prior to administration of a combination of olopatadine and mometasone as described herein, the skin prick test was performed on the subject and resulted in a wheal diameter of at least 3 mm greater than a negative control such as saline.

The methods of treatment described herein can be administered to a subject without the subject exhibiting any significant treatment-related adverse effects, for example, after 1 or 2 weeks treatment.

The treatment related adverse effects in the context of the present invention may include, but are not limited to, eye disorders (e.g., conjunctivitis), gastrointestinal disorders (e.g., abdominal distension, diarrhoea, dyspepsia, dysphagia and gastric ulcer, haemorrhoidal haemorrhage, hyperchlorhydria, nausea and vomiting, and toothache), general disorders (e.g., fatigue, local swelling, peripheral oedema, pain and pyrexia), infections and infestations (e.g., oral herpes and upper respiratory tract infection), injury, poisoning and procedural complications, musculoskeletal and connective tissue disorders (e.g., arthralgia), nervous system disorders (e.g., disturbance in attention, dizziness, dysgeusia, somnolence and headache), reproductive system and breast disorder (e.g., dysmenorrhea) respiratory, thoracic and mediastinal disorders (e.g., epistaxis, dry throat, dyspnea, epistaxis, nasal congestion, nasal discomfort, respiratory tract haemorrhage, rhinorrhea, throat irritation, and upper-airway cough syndrome), skin and subcutaneous tissue disorders (e.g., rash and urticaria).

In another embodiment, the present invention relates to a method of treating seasonal allergic rhinitis and/or nasal symptoms associated with seasonal allergic rhinitis in a subject (e.g., a human) in need thereof comprising nasally administering to the subject a synergistic combination comprising mometasone furoate and olopatadine hydrochloride, wherein the combination is in the form of a pharmaceutical composition comprising mometasone furoate and olopatadine hydrochloride in a weight ratio of about 1:5 to about 1:60 or from about 1:13.3 to about 1:53.2 (based on the equivalent weight of olopatadine free base).

Synergistic effects for the combination of mometasone furoate and olopatadine hydrochloride can be evaluated by various methods. One method for evaluating the efficacy of an agent for treating allergic rhinitis is the ovalbumin induced rhinitis model in guinea pigs. In such models, the effect of the treatment is studied in animals sensitized and challenged with ovalbumin, followed by detailed analysis of their sneezing response using whole body plethysmography and the total number of eosinophils in a nasal lavage sample.

The fixed-dose pharmaceutical composition comprising mometasone or its salt and olopatadine or its salt may be administered to the subject according to one of the following regimens:

a) the composition is nasally administered as 1 spray per nostril once daily for a period of at least 1 week;
b) the composition is nasally administered as 2 sprays per nostril once daily for a period of at least 1 week;
c) the composition is nasally administered as 1 spray per nostril twice daily for a period of at least 1 week;

d) the composition is nasally administered as 2 sprays per nostril twice daily for a period of at least 1 week;

e) the composition is nasally administered as 1 spray per nostril once daily for a period of 2 weeks;

f) the composition is nasally administered as 2 sprays per nostril once daily for a period of 2 weeks;

g) the composition is nasally administered as 1 spray per nostril twice daily for a period of 2 weeks; or h) the composition is nasally administered as 2 sprays per nostril twice daily for a period of 2 weeks.

In another embodiment, the present invention relates to a method of treating seasonal allergic rhinitis and/or nasal symptoms associated with seasonal allergic rhinitis in a human in need thereof comprising nasally administering to the human a synergistic combination comprising mometasone furoate and olopatadine hydrochloride, wherein the combination is in the form of a pharmaceutical composition comprising mometasone furoate in particulate form and olopatadine hydrochloride in solution in a weight ratio of about 1:13.3 to about 1:53.2 (based on the equivalent weight of olopatadine free base), and wherein the composition is administered as 1 or 2 sprays per nostril of the human, at least once daily for a period of at least 1 week wherein the method provides reduction of at least one treatment-related adverse effect. In one aspect of this embodiment, the composition is administered once daily or twice daily for a period of 2 weeks. In another aspect of this embodiment, each spray comprises about 25 mcg or about 50 mcg of mometasone furoate and about 665 mcg of olopatadine hydrochloride. In yet another aspect of this embodiment, (i) the total nasal symptoms score (TNSS) of the human is reduced by at least 50% from baseline after 2 weeks treatment, and/or (ii) total ocular symptom score (TOSS) of the human is reduced by at least 40% from baseline after 2 weeks treatment, and/or (iii) no significant treatment-related adverse effects are observed in the human after 2 weeks treatment. In one aspect of the said embodiment, the human exhibits a positive skin prick test to an allergen. Preferably, the treatment-related adverse effects include somnolence or epistaxis or a combination thereof.

In an aspect of the invention, the fixed-dose pharmaceutical composition may be administered for a period of about 1 week, 2 weeks, 4 weeks, 6 weeks or 8 weeks. Preferably, the fixed-dose pharmaceutical composition, is administered as 1 or 2 sprays per nostril of the subject (e.g., a human), once daily or twice daily for a period of 1 week or 2 weeks. In another aspect of the embodiment, each spray of the composition comprises olopatadine hydrochloride equivalent to about 600 mcg of olopatadine and about 25 mcg to about 50 mcg of mometasone furoate. Preferably, each spray of the composition comprises about 665 mcg of olopatadine hydrochloride (equivalent to about 600 mcg of olopatadine) and about 25 mcg or about 50 mcg of mometasone furoate. In yet another aspect, the composition does not have unpleasant odor and taste. In yet another aspect of the embodiment, the total nasal symptoms score (TNSS) of the human subject is reduced by at least 40% or at least 50% from baseline after 1 or 2 weeks treatment. In yet another aspect of the embodiment, the total ocular symptom score (TOSS) of the human is reduced by at least 30% or at least 40% from baseline after 1 or 2 weeks treatment. In yet another aspect of the embodiment, the said method provides reduction in treatment-related adverse effects. Preferably, the treatment-related adverse effects include somnolence or epistaxis or a combination thereof. In yet another aspect of the embodiment, the human subject is a patient exhibiting a positive skin prick test to an allergen.

In one aspect the present invention relates to the use of mometasone or its salt and olopatadine or its salt in a weight ratio of about 1:5 to about 1:60 or from about 1:12 to about 1:53 for the manufacture of a fixed-dose pharmaceutical composition of the invention for the treatment of allergic rhinitis in a subject (e.g., a human) in need thereof. In an aspect, the fixed-dose pharmaceutical composition is a suspension wherein mometasone or its salt is present in particle form (e.g., having a mean particle size of from about 1 to about 20 µm, or from about 1 to about 15 µm) and olopatadine or its salt is present in dissolved form. In yet another aspect, the composition does not have unpleasant odor and taste.

In a separate embodiment the present invention relates to a method of reducing symptoms associated with rhinitis in a subject (e.g. a human) in need thereof, the method comprising nasally administering to the subject an effective amount of a fixed dose pharmaceutical composition comprising mometasone or its salt and olopatadine or its salt in a weight ratio of about 1:5 to about 1:60 or from about 1:12 to about 1:53 for about 1 or 2 weeks.

In yet another embodiment, the present invention relates to a method of reducing symptoms associated with allergic rhinitis in a human in need thereof comprising nasally administering to the human an effective amount of a fixed-dose pharmaceutical composition comprising mometasone or its salt and olopatadine or its salt, wherein (i) the composition is nasally administered as 1 or 2 sprays per nostril of the human at least once daily, and (ii) each spray comprises mometasone or its salt and olopatadine or its salt in a weight ratio of about 1:5 to about 1:60 or from about 1:12 to about 1:53 for about 1 or 2 weeks. (based on the equivalent weight of olopatadine free base) and wherein the composition is administered as 1 or 2 sprays per nostril of the human, at least once daily for a period of at least 1 week, wherein the method provides reduction of at least one treatment-related adverse effect. In one aspect of this embodiment, each spray comprises about 25 mcg or about 50 mcg mometasone furoate and olopatadine hydrochloride equivalent to about 600 mcg olopatadine. In one aspect of this embodiment, the pharmaceutical composition is a suspension comprising mometasone or its salt in particulate form and olopatadine or its salt in solution. In one aspect of this embodiment, the composition is administered for a period of at least 1 week as—(i) 1 spray per nostril once daily or twice daily, or (ii) 2 sprays per nostril once daily or twice daily. In yet another aspect of this embodiment, the allergic rhinitis is selected from perennial allergic rhinitis, persistent allergic rhinitis, seasonal allergic rhinitis, and nasal and/or non-nasal symptoms associated therewith. In a preferred aspect, the allergic rhinitis is seasonal allergic rhinitis and/or nasal symptoms associated therewith. In yet another aspect of this embodiment, (i) the total nasal symptoms score (TNSS) of the human is reduced by at least 50% from baseline after 2 weeks treatment, and/or (ii) total ocular symptom score (TOSS) of the human is reduced by at least 40% from baseline after 2 weeks treatment, and/or (iii) no significant treatment-related adverse effects are observed in the human after 2 weeks treatment. In one aspect of the said embodiment, the human exhibits a positive skin prick test to an allergen. In one aspect of the said embodiment, the symptoms include rhinorrhea, nasal congestion, nasal itching, sneezing, itching/burning eyes, tearing/watering eyes, redness of eyes, itching of ears or palate, coughing, ocular pruritus, excess lacrimation, headache, fatigue and malaise.

In yet another aspect of the embodiment, the treatment-related adverse effects include somnolence or epistaxis or a combination thereof.

Another embodiment relates to a method of reducing eosinophil count in the nasal lavage of a subject by nasally administering an effective amount of a fixed-dose pharmaceutical composition comprising mometasone or its salt and olopatadine or its salt in a weight ratio of about 1:5 to about 1:60 (based on the equivalent weight of olopatadine free base), wherein the method provides a greater reduction in eosinophil count than that provided by mometasone or its salt or olopatadine or its salt when administered as a monotherapy. The eosinophil count can be measured by any known technique, such as with a hemocytometer.

Yet another embodiment relates to a method of reducing total cell count in the nasal lavage by nasally administering an effective amount of a fixed-dose pharmaceutical composition comprising mometasone or its salt and olopatadine or its salt in a weight ratio of about 1:5 to about 1:60 (based on the equivalent weight of olopatadine free base) wherein the method provides a greater reduction in total cell count than that provided by mometasone or its salt or olopatadine or its salt when administered as a monotherapy.

In the context of the present invention, eosinophil count and total cell count can be measured using various instruments such as a hemocytometer. Sneezing response can be determined using instruments such as a whole body plethysmography (Buxco Research Systems, Wilmington, N.C., USA).

In the context of the present invention, the fixed dose pharmaceutical composition comprising mometasone or its salt, olopatadine or its salt are preferably supplied in the form of nasal spray with one or more pharmaceutical acceptable excipients (e.g., chelating agents, preservatives, buffer, surfactants, isotonic agent, taste masking agents, suspending agents, humectants, antioxidants and diluents) in a container and a kit providing directions on its usage and administration. The pharmaceutical composition may, for example, have any one of the formulations described in International Patent Application No. PCT/IB2014/064251, filed Sep. 4, 2014, U.S. patent application Ser. No. 14/483,837, filed Sep. 11, 2014, or U.S. patent application Ser. No. 14/662,128, filed Mar. 18, 2015, each of which is hereby incorporated by reference in its entirety.

The pharmaceutical composition can be nasally administered with a nasal spray device (e.g., one capable of delivery a mist spray in the nostrils of a subject for local action on nasal mucosa).

The following examples are provided to enable one skilled in the art to practice the invention and these are merely illustrative of the invention and should not be read as limiting the scope of the invention.

EXAMPLES

Example 1

Effect of Mometasone and Olopatadine and their Combination on Ovalbumin Induced Rhinitis Model in Male Guinea Pigs Male Dunkin Hartley guinea pigs were actively sensitized with a subcutaneous injection of 1.5 mg of ovalbumin and 20 mg of aluminum hydroxide gel on days 0 and 7. Guinea pigs were sensitized intranasally with 2% ovalbumin from days 14-17. On day 28, the animals were challenged with 6% ovalbumin intranasally.

Animal Grouping

Actively sensitized animals were randomly assigned to one of the following 5 groups during the experiment (see Table 1).

A: Saline Control (vehicle treated/saline challenged),

B: Ovalbumin Control (vehicle treated/ovalbumin challenged),

C: Olopatadine hydrochloride 50 µg (based on the equivalent weight of olopatadine free base) (olopatadine hydrochloride 50 µg treated/ovalbumin challenged), D: Mometasone furoate 10 µg (mometasone furoate 10 µg treated/ovalbumin challenged) and E: Combination (mometasone furoate 10 µg+olopatadine hydrochloride 50 µg (based on the equivalent weight of olopatadine free base) treated/ovalbumin challenged).

Compound Administration

Mometasone furoate 10 µg was given intranasally 24 hours and 1 hour prior to the final ovalbumin challenge. Olopatadine hydrochloride was given intranasally 1 hour before the final ovalbumin challenge. The dosing volume was 40 µl/animal. The saline control group and ovalbumin control group received vehicle (40 µl, 0.1% Tween 80 in distilled water).

TABLE 1

Animal Groups

| Group | Group Code | Treatment | Ovalbumin Challenge | Animals/ group |
|---|---|---|---|---|
| A | Saline Control | Vehicle | − | 6 |
| B | Ovalbumin Control | Vehicle | + | 7 |
| C | Olopatadine 50 µg | Olopatadine Hydrochloride 50 µg | + | 7 |
| D | Mometasone 10 µg | Mometasone Furoate 10 µg | + | 6 |
| E | Combination | Olopatadine Hydrochloride 50 µg + Mometasone Furoate 10 µg | + | 7 |

In Vivo Evaluation Measurement of Sneezing Response

Sneezing response was determined by using whole body plethysmography (Buxco Research Systems, USA) for 50 minutes after final saline or ovalbumin challenge.

Nasal Lavage

Nasal lavage was performed at 4 hours after challenge of animals with saline or ovalbumin on day 28. Animals were anesthetized with an overdose of urethane, the trachea was exposed and nasal lavage was performed using 2 mL prewarmed normal saline. The collected nasal lavage was taken for total cell count using a hemocytometer. The nasal lavage was centrifuged, and the cell pellet resuspended in 15 µL guinea pig serum and used for preparation of smears. Slides were stained with Leishman's stain and a differential cell count of 100 cells based on standard morphology was performed manually.

Calculations

The total number of eosinophils in each nasal lavage sample was calculated using the formula:

$$\text{Total No. of eosinophils (in nasal lavage)} = \frac{\text{Total cell count} \times 10^5/\text{mL} \times \text{Percent eosinophils}}{100}$$

Percent inhibition of eosinophils was calculated using the following formula:

$$\% \text{ Inhibition of eosinophils} = \frac{\text{Avg. eosinophils}_{(Ovalbumin\ control)} - \text{eosinophils}_{(compound)}}{\text{Avg. eosinophils}_{(Ovalbumin\ control)} - \text{Avg. eosinophils}_{(Saline\ Control)}} \times 100$$

Data analysis Data was statistically analyzed using one way ANOVA followed by Dunnett's multiple comparison tests.

Results

Figure 1:
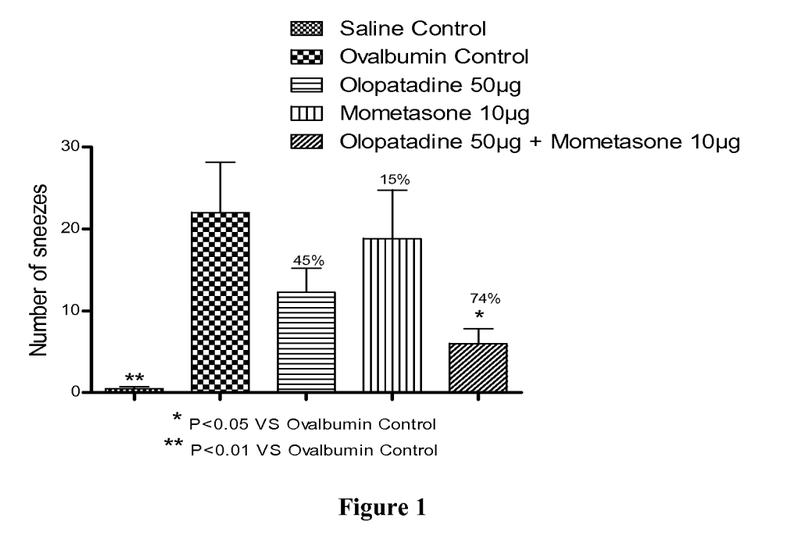
FIG. 1 is a bar graph depicting the effect of a saline control, ovalbumin control, olopatadine hydrochloride (equivalent to 50 μg olopatadine base), mometasone furoate (10 μg), and a combination of mometasone furoate (10 μg) and olopatadine hydrochloride (equivalent to 50 μg olopatadine base) on the sneezing response in guinea pigs as described in Example 1.
Figure 2:
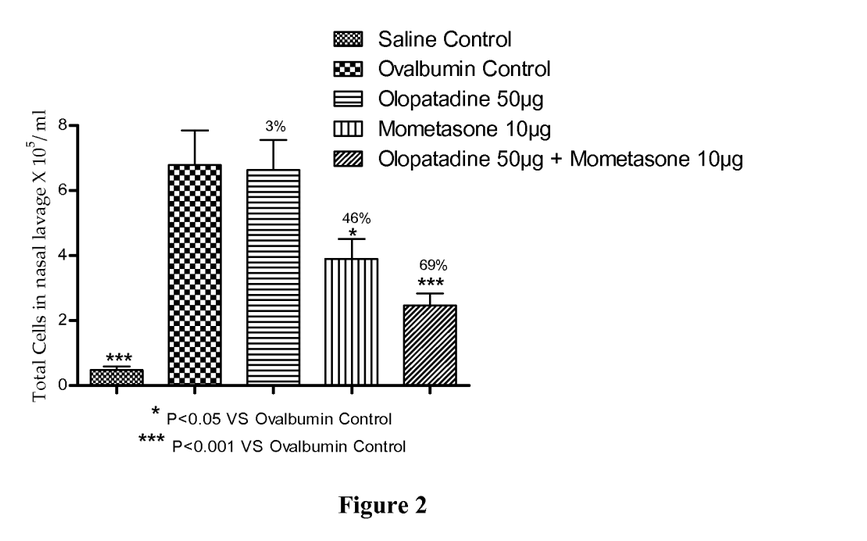
FIG. 2 is a bar graph depicting the effect of a saline control, ovalbumin control, olopatadine hydrochloride (equivalent to 50 μg olopatadine base), mometasone furoate (10 μg), and a combination of mometasone furoate (10 μg) and olopatadine hydrochloride (equivalent to 50 μg olopatadine base) on total cell count in the nasal lavage of guinea pigs as described in Example 1.
Figure 3:
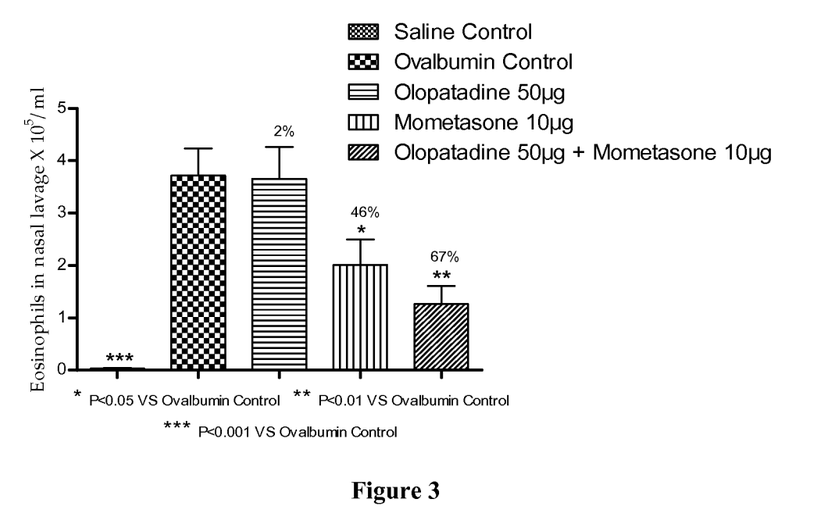
FIG. 3 is a bar graph depicting the effect of a saline control, ovalbumin control, olopatadine hydrochloride (equivalent to 50 μg olopatadine base), mometasone furoate (10 μg), and a combination of mometasone furoate (10 μg) and olopatadine hydrochloride (equivalent to 50 μg olopatadine base) on the number of eosinophils in the nasal lavage of guinea pigs as described in Example 1.

Mometasone furoate monotherapy showed significant inhibition of total cell and eosinophils in nasal lavage but was not effective in inhibiting sneezing response. Olopatadine hydrochloride monotherapy did not show significant inhibition of any of the parameters in this model. The combination of mometasone furoate with olopatadine hydrochloride showed synergy for inhibition of sneezing response (FIG. 1), cellular infiltration in nasal lavage (FIG. 2) and nasal eosinophilia (FIG. 3) as compared to respective monotherapy arms (see Table 2).

TABLE 2

Summary of the effects of a combination of mometasone furoate and olopatadine hydrochloride on ovalbumin induced rhinitis model in guinea pigs.

| Treatment | Saline control | Ovalbumin control | Olopatadine Hydrochloride (OH) | Mometasone Furoate (MF) | Combination (OH & MF)) |
|---|---|---|---|---|---|
| Dose (μg per animal) | — | — | 50 | 10 | 50 (OH) & 10 (MF) |
| Number of Sneeze (0-50 min) | 0.5** | 22 | 12.29 | 18.83 | 6* |
| Percent inhibition of sneeze | — | — | 45 | 15 | 74 |
| Total cell count × $10^5$/ml nasal lavage | 0.48*** | 6.79 | 6.63 | 3.90* | 2.46*** |
| Percent inhibition of total cell count | — | — | 3 | 46 | 69 |
| Eosinophils × $10^5$/ml nasal lavage | 0.03*** | 3.71 | 3.64 | 2.00* | 1.26** |
| % inhibition of eosinophils | — | — | 2 | 46 | 67 |

*P < 0.05 vs. Ovalbumin Control,
**P < 0.01 vs. Ovalbumin Control,
***P < 0.001 vs. Ovalbumin control The combination of mometasone furoate and olopatadine hydrochloride showed a beneficial effect greater than the individual monotherapies. The combination of mometasone furoate and olopatadine hydrochloride showed synergy in the treatment of allergic rhinitis in this model.

Example 2

Effect of Mometasone and Olopatadine and their Combination on Ovalbumin Induced Rhinitis Model in Male Guinea Pigs The procedure in Example 1 was repeated except 120 μg of olopatadine hydrochloride (based on the equivalent weight of olopatadine free base) was used. The animal groups in Table 3 below were used during this experiment.

TABLE 3

Animal Groups

| Group | Group Code | Treatment | Ovalbumin Challenge | Animals/group |
|---|---|---|---|---|
| A | Saline Control | Vehicle | − | 9 |
| B | Ovalbumin Control | Vehicle | + | 10 |
| C | Olopatadine 120 μg | Olopatadine Hydrochloride 120 μg | + | 10 |
| D | Mometasone 10 μg | Mometasone Furoate 10 μg | + | 9 |
| E | Combination | Olopatadine Hydrochloride 120 μg + Mometasone Furoate 10 μg | + | 10 |

Compound administration was performed as in Example 1, except the dosing volume was 60 μl/animal. The saline control group and ovalbumin control group received vehicle (60 μl, 0.1% Tween 80 in distilled water). In vivo evaluations were performed as in Example 1.

Results

Figure 4:
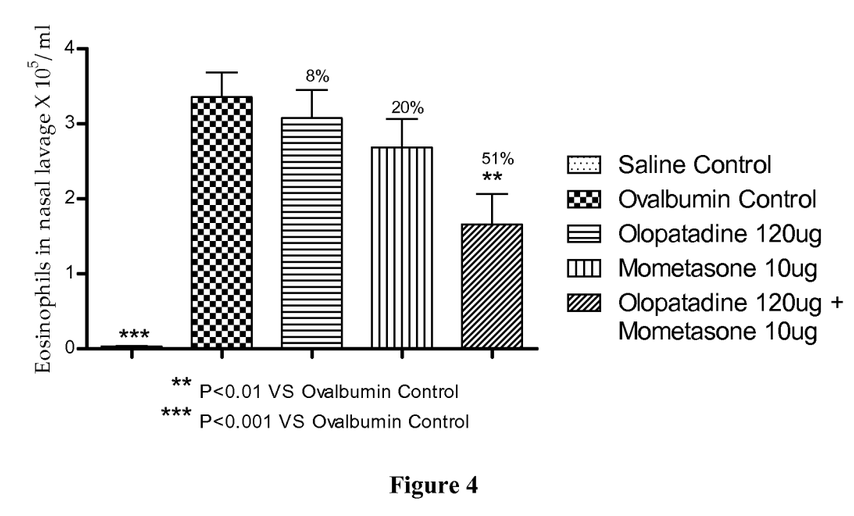
FIG. 4 is a bar graph depicting the effect of a saline control, ovalbumin control, olopatadine hydrochloride (equivalent to 120 μg olopatadine base), mometasone furoate (10 μg), and a combination of mometasone furoate (10 μg) and olopatadine hydrochloride (equivalent to 120 μg olopatadine base) on the number of eosinophils in the nasal lavage of guinea pigs as described in Example 2.
Figure 5:
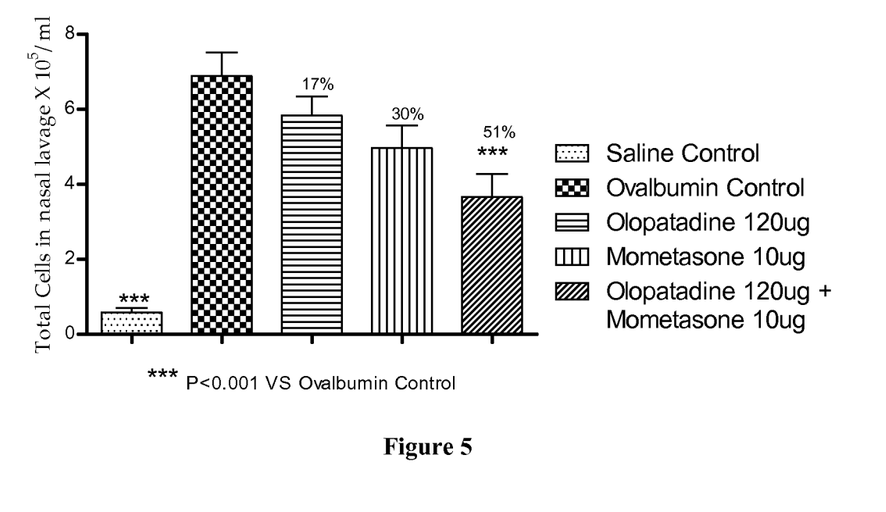
FIG. 5 is a bar graph depicting the effect of a saline control, ovalbumin control, olopatadine hydrochloride (equivalent to 120 μg olopatadine base), mometasone furoate (10 μg), and a combination of mometasone furoate (10 μg) and olopatadine hydrochloride (equivalent to 120 μg olopatadine base) on the total cell count in the nasal lavage of guinea pigs as described in Example 2.
Figure 6:
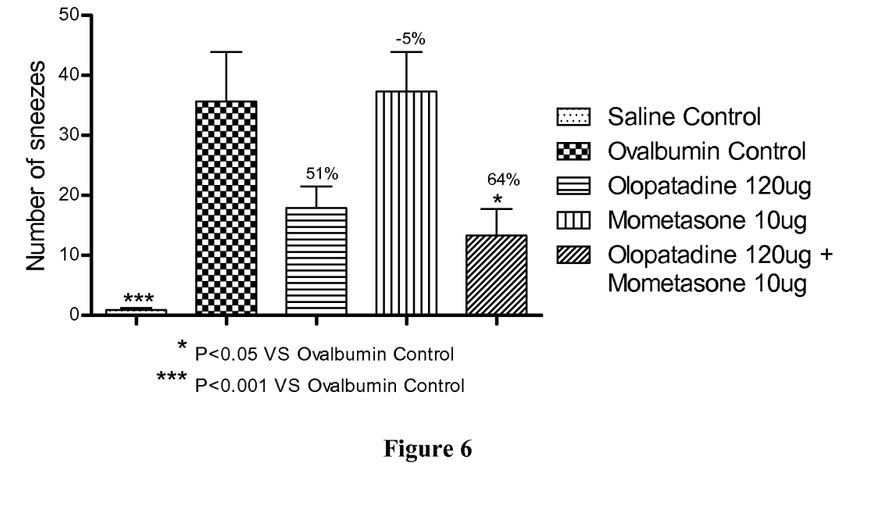
FIG. 6 is a bar graph depicting the effect of a saline control, ovalbumin control, olopatadine hydrochloride (equivalent to 120 μg olopatadine base), mometasone furoate (10 μg), and a combination of mometasone furoate (10 μg) and olopatadine hydrochloride (equivalent to 120 μg olopatadine base) on the sneezing response in guinea pigs as described in Example 2.

Mometasone monotherapy showed significant inhibition of total cell and eosinophils in nasal lavage but was not effective in inhibiting sneezing response. Olopatadine monotherapy did not show significant inhibition of any of the parameter in this model. The combination of mometasone with olopatadine showed synergy for the inhibition of nasal eosinophilia, cellular infiltration in nasal lavage and sneezing response as compared to the respective monotherapies (see FIGS. 4-6 and Table 4).

TABLE 4

Summary of the effects of combination of mometasone and olopatadine on ovalbumin induced rhinitis model in guinea pigs

| Treatment | Saline control | Ovalbumin control | Olopatadine Hydrochloride (OH) | Mometasone Furoate (MF) | Combination (OH & MF) |
|---|---|---|---|---|---|
| Dose (μg per animal) | — | — | 120 | 10 | 120 (OH) & 10 (MF) |
| Number of Sneeze (0-50 min) | 0.89*** | 35.70 | 17.90 | 37.33 | 13.30* |
| Percent inhibition of sneeze | — | — | 51 | −5 | 64 |
| Total cell count × $10^5$/ml nasal lavage | 0.58*** | 6.88 | 5.83 | 4.96 | 3.66*** |
| Percent inhibition of total cell count | — | — | 17 | 30 | 51 |
| Eosinophils × $10^5$/ml nasal lavage | 0.03*** | 3.36 | 3.08 | 2.69 | 1.66** |
| % inhibition of eosinophils | — | — | 8 | 20 | 51 |

*$P < 0.05$ vs. Ovalbumin Control,
**$P < 0.01$ vs. Ovalbumin Control,
***$P < 0.001$ vs. Ovalbumin Control The combination of mometasone furoate and olopatadine hydrochloride showed a beneficial effect greater than the individual monotherapies. The combination of mometasone and olopatadine showed synergy in this guinea pig rhinitis model.

Example 3

Clinical Study of Fixed Dose Combination of Mometasone and Olopatadine Nasal Spray in Human Patients The study was a single-centre, double blind, double-dummy, randomized, parallel-group, comparative Environmental Exposure Chamber (EEC) study to evaluate the efficacy, safety and tolerability of (i) two fixed dose combination products of mometasone furoate and olopatadine hydrochloride nasal spray, (ii) a fixed dose combination of azelastine hydrochloride and fluticasone propionate nasal spray (DYMISTA®), (iii) olopatadine nasal spray (PATANASE®), and (iv) a placebo nasal spray in patients with seasonal allergic rhinitis (SAR).

Key Objectives

To evaluate the efficacy of two strengths of the fixed dose combination (FDC) of mometasone furoate and olopatadine hydrochloride nasal spray when compared with a placebo nasal spray.

To evaluate the comparative efficacy of (i) two regimens of FDC products containing mometasone furoate and olopatadine hydrochloride nasal spray, (ii) a fixed dose combination of azelastine hydrochloride and fluticasone propionate nasal spray (DYMISTA®), and (iii) Olopatadine nasal spray (PATANASE®).

To compare the efficacy of (i) a fixed dose combination of azelastine hydrochloride and fluticasone propionate nasal spray and (ii) olopatadine nasal spray, when compared with a placebo nasal spray.

To compare the onset of action between active treatments groups after the first dose defined as "the first time point after initiation of treatment when the drug demonstrates a significant reduction in instantaneous TNSS compared to the placebo treatment that proves durable from this point."

To compare the EEC-Quality of Life Questionnaire (QoLQ) and tolerability and acceptability between a fixed dose combination of mometasone furoate and olopatadine hydrochloride once daily and a fixed dose combination of mometasone furoate and olopatadine hydrochloride twice daily.

To evaluate the comparative safety between the various treatment arms.

Sample Size

A total of 36 patients per treatment arm were randomized in the study. The total number of randomized subjects throughout the five treatment arms was 180.

Patient Population

Subjects suffering from seasonal allergic rhinitis for the last two years that require treatment either with intranasal antihistamines and/or intranasal steroids were included in the study.

Key Subject Selection Criteria

1. Patients age ≥18 and ≤65 years inclusive of either sex;

2. Patient with a known clinical history of seasonal allergic rhinitis (for at least 2 years) and exhibiting a positive skin prick test (wheal diameter at least 3 mm greater than saline control) to one of the regional allergens;

3. Patients with the ability to understand and sign a written informed consent form, which must have been obtained prior to screening; and 4. Patients willing to comply with the protocol requirements.

Study Design

Patients were randomized to treatment in a 1:1:1:1:1 ratio to the following five treatment arms, at one study site:

1. Fixed dose combination of olopatadine hydrochloride 665 mcg and mometasone furoate 25 mcg twice daily (BID)

2. Fixed dose combination of olopatadine hydrochloride 665 mcg and mometasone furoate 50 mcg once daily (QD)

3. DYMISTA® nasal spray (azelastine hydrochloride 137 mcg+fluticasone propionate 50 mcg) Spray twice daily (BID)

4. PATANASE® nasal spray (olopatadine hydrochloride 665 mcg) twice daily (BID)

5. Placebo nasal spray

The double-dummy design including four masked nasal spray bottles (two for evening dosing and two for morning dosing) were utilized for this study (see Table A).

TABLE A

Treatment Administration Using Four Masked Bottles of Nasal Sprays

| | Treatment Arm | Morning | | Evening | |
|---|---|---|---|---|---|
| | | $1^{st}$ bottle | $2^{nd}$ bottle | $1^{st}$ bottle | $2^{nd}$ bottle |
| 1 | TP-1: Fixed dose combination of mometasone furoate 25 mcg + olopatadine hydrochloride 665 mcg twice daily (BID) | Active | Active | Active | Active |
| 2 | TP-2: Fixed dose combination of mometasone furoate 50 mcg + olopatadine hydrochloride 665 mcg once daily (QD) | Active | Active | Placebo | Placebo |
| 3 | DYMISTA ® twice daily (BID) | Placebo | Active | Placebo | Active |
| 4 | PATANASE ® twice daily (BID) | Active | Active | Active | Active |
| 5 | Placebo | Placebo | Placebo | Placebo | Placebo |

This study consisted of five visits to the study site and a 12 day at-home dosing period (and 2 days of onsite dosing—a total of 14 days of dosing). Assessment of efficacy endpoints were done out of season, in an EEC facility. After the initial screening visit (Visit 1), patients who met all study criteria (including the main criteria for inclusion: a positive skin prick test (SPT) and a 2 year medical history of allergic rhinitis (AR) to ragweed allergen) underwent further screening/priming in the EEC (Visit 2). During the EEC session patients were exposed to ragweed pollen at a concentration of 3500±500 particles/m³ for 6 hours. Patients used an electronic diary (ePDAT™) to rate their ocular and nasal symptoms every 30 minutes in the EEC Patients who met a minimum qualifying TNSS of 6/12, including a score of at least 2 for nasal congestion on two consecutive diary entries continued in the study. At Visit 3, on the following day (Day 1), patients who met the minimum criteria returned to the EEC for a second consecutive EEC session. Patients were exposed to allergen for approximately 10 hours during this visit. During the first 6 hours, patients used the electronic diary to complete symptom assessments every 30 minutes and met the minimum qualifying symptom score in order to continue. Those who met the minimum qualifying symptom score were randomized to receive one of the five study drugs after the 6 hours time point in the EEC. After dosing (at approximately noon), patients were asked to complete symptom assessments at 5 minute, 10 minutes, 15 minutes, 25 minutes, 30 minute, 45 minutes, 60 minutes and then every 30 minutes for the remainder of the visit Post-treatment symptom assessments in the EEC were used to determine onset of action for study treatments. Patients were then sent home with their study medication to continue at-home BID dosing starting from the evening dose for Day 1. Patients continued at-home dosing for a period of 12 days. Following the 12 days (Days 2-13) of at-home dosing, patients returned to the EEC on Day 14 (Visit 4) for a post-treatment 6-hour priming EEC session. Patients were dosed with the morning dose of study drug one hour prior to entering the EEC. Symptoms were assessed every 30 minutes in the EEC Patients took their last dose of study treatment at midnight on the same day, and returned on the following morning (Day 15, Visit 5) for a 6 hour EEC session Over a period of 6 hours, patients used the electronic diary to complete symptom assessments every 30 minutes. In addition to collection of nasal and ocular symptoms, the electronic diary was used to collect EEC-Quality-of-Life Questionnaires (EEC-QoLQ) at Visits 2, 3, 4 and 5, and acceptability and tolerability at Visit 5. Visit 5 was the final visit for the study.

Priming

Fulfillment of the following criteria on each of two consecutive diary cards reading at priming visit: minimum TNSS of 6 out of 12, including a score of at least 2 for nasal congestion.

Randomization

Patients meeting these same criteria at both priming visits of 3 hours chamber duration in order to proceed to the treatment visit (Visit 3).

At the treatment visit (Visit 3), a minimum TNSS of 6 out of 12 (including a score of at least 2 for nasal congestion).

Drug Formulations

The test product formulations used in the study were as follows:

Test Product 1 (TP-1)

Mometasone Furoate Monohydrate and Olopatadine Hydrochloride Nasal Spray (25 mcg+600 mcg)

Each spray delivered mometasone furoate monohydrate equivalent to 25 mcg mometasone furoate and olopatadine hydrochloride equivalent to 600 mcg olopatadine.

Test Product 2 (TP-2)

Mometasone Furoate Monohydrate and Olopatadine Hydrochloride Nasal Spray (50 mcg+600 mcg)

Each spray delivered mometasone furoate monohydrate equivalent to 50 mcg mometasone furoate and olopatadine hydrochloride equivalent to 600 mcg olopatadine.

Dosage Regimen

1. Investigational Products

TP-1: Fixed dose combination of Olopatadine hydrochloride (665 mcg) and Mometasone furoate (25 mcg) Nasal Spray: 2 sprays per nostril were delivered Twice daily (BID) for two weeks.

TP-2: Fixed dose combination of Olopatadine hydrochloride (665 mcg) and Mometasone furoate (50 mcg) Nasal Spray: 2 sprays per nostril were delivered once daily (QD) for two weeks 2. Reference Therapies Olopatadine hydrochloride Nasal Spray (PATANASE® 0.6%): 2 sprays per nostril were delivered twice daily for two weeks.

DYMISTA® (azelastine hydrochloride+fluticasone propionate) 137 mcg/50 mcg Nasal Spray: 1 spray per nostril was delivered twice daily for two weeks.

Placebo Nasal Spray (based on vehicle of Investigational product): 2 sprays per nostril were delivered twice daily for two weeks.

Key Evaluation Criteria (Clinical Endpoints)

Change from baseline in mean post-treatment Total Nasal Symptoms Score (TNSS) over placebo for fixed dose combination of mometasone furoate and olopatadine hydrochloride. Mean TNSS were calculated over 6 hours in the EEC for post-treatment at Visit 5 (over hours 18 to 24 after the first dosing on Day 14) and matched baseline TNSS in the EEC at Visit 3 (over 6 hours prior to first dosing).

Change from baseline in mean post-treatment TNSS for two regimens of fixed dose combination of mometasone furoate and olopatadine hydrochloride with reference products: DYMISTA® nasal spray and PATANASE® nasal spray. Mean TNSS were calculated over 6 hours in the EEC for post-treatment at Visit 5 (over hours 18 to 24 after the first dosing on Day 14) and matched baseline TNSS in the EEC at Visit 3 (over 6 hours prior to first dosing).

Change from baseline in mean post-treatment TNSS for two regimens of fixed dose combination of mometasone furoate and olopatadine hydrochloride, DYMISTA® nasal spray and PATANASE® nasal spray. Mean post-treatment TNSS were calculated over 6 hours in the EEC for post-treatment at Visit 4 (over hours 1 to 7 after first dosing on Day 14) and matched baseline TNSS in the EEC at Visit 2 (over 6 hours).

Change from baseline in mean post-treatment TNSS for two regimens of fixed dose combination of mometasone furoate and olopatadine hydrochloride compared with reference products: DYMISTA® nasal spray and PATANASE® nasal spray. Mean TNSS were calculated over 12 hours in the EEC for post-treatment (at Visit 4 over 1 to 7 hours after first dosing on Day 14, and at Visit 5 over 18 to 24 hours after first dosing on Day 14) and matched baseline TNSS in the EEC at Visit 2 and Visit 3 (over 12 hours prior to first dosing).

Onset of Action for each treatment of fixed dose combination of mometasone furoate and olopatadine hydrochloride, DYMISTA® and PATANASE® were assessed by comparing change from baseline in post-treatment TNSS between each active treatment and placebo at every time point after the first treatment.

Change from baseline in TNSS were calculated at every time point after the first dose of study treatment in the EEC at Visit 3 (i.e., over the last four hours in the EEC at Visit 3) with baseline (Visit 3) defined as the average of the last two time points pre-dosing.

Change from baseline in mean post-treatment Total Symptoms Score (TSS), Individual Nasal Symptoms Scores (NSS, four nasal symptoms of rhinorrhea, pruritus, sneezing and nasal congestion) and TOSS over 6 hours in the EEC at Visit 5 and matched baseline at Visit 3 (over 6 hours prior to first dosing).

Change from baseline in mean post-treatment Total Symptoms Score (TSS), Individual Nasal Symptoms Scores (NSS, four nasal symptoms of rhinorrhea, pruritus, sneezing and nasal congestion) and TOSS over the 6 hours in the EEC at Visit 4 and matched baseline at Visit 2 (over the 6 hours in the EEC).

Change from baseline in mean post-treatment Total Symptoms Score (TSS), Individual Nasal Symptoms Scores (NSS, four nasal symptoms of rhinorrhea, pruritus, sneezing and nasal congestion) and TOSS over 12 hours in the EEC at Visit 4 and Visit 5 and matched baseline over 12 hours in the EEC prior to dosing at Visit 2 and Visit 3.

EEC-QoLQ for all treatment arms by comparing 1) pre-EEC-QoLQ at baseline (Visit 2) with pre-EEC at Visit 4; 2) post-EEC at baseline Visit 2 with post-EEC at Visit 4; 3) after 6 hours in the EEC at Visit 3 (prior to first dosing) with post-EEC at Visit 5.

Reflective tolerability and acceptability for treatment arms compared to placebo post-EEC at Visit 5.

Results

Table B shows a summary of the TNSS change from baseline to post-treatment over 6 hours in EEC (ITT Population).

TABLE B

| Parameters | Placebo | TP-1 | TP-2 | DYMISTA® (Reference) | PATANASE® (Reference) |
|---|---|---|---|---|---|
| Baseline EEC N | 36 | 36 | 36 | 36 | 36 |
| Baseline EEC Mean | 7.64 | 8.07 | 8.20 | 8.67 | 8.27 |
| EEC at the end of treatment (2 weeks) Mean | 6.61 | 3.31 | 3.94 | 4.80 | 6.38 |
| % Change from Baseline | — | 13.35 | 58.98 | 51.95 | 45.67 | 22.85 |

Table C shows a summary of the TNSS change from baseline to post-treatment over 12 hours in EEC (ITT Population). (The data for NASONEX in Table C is sourced from its U.S. FDA approved label.)

TABLE C

| Parameters | TP-1 | TP-2 | PATANASE® (Reference) | NASONEX®* | DYMISTA® (Reference) |
|---|---|---|---|---|---|
| N | 36 | 36 | 36 | 176 | 36 |
| Baseline EEC Mean | 7.58 | 7.85 | 7.90 | 9.60 | 8.25 |
| EEC at the end of treatment (2 weeks) Mean | 2.85 | 3.36 | 5.72 | — | 4.34 |
| % Change from Baseline | — | 62.4 | 57.07 | 27.5 | 27.92 | 48.24 |

*NASONEX® (mometasone furoate nasal spray) US FDA Approved label (Jan. 19, 2011)

Table D shows a summary of the TOSS change from baseline to post-treatment over 12 hours in EEC (ITT Population).

TABLE D

| Parameters | TP-1 | TP-2 | PATANASE® (Reference) | DYMISTA® (Reference) |
|---|---|---|---|---|
| N | 36 | 36 | 36 | 36 |
| Baseline EEC Mean | 3.97 | 4.17 | 3.92 | 4.54 |
| EEC at the end of treatment (2 weeks) Mean | 1.97 | 2.34 | 2.82 | 2.82 |

TABLE D-continued

| Parameters | TP-1 | TP-2 | PATANASE ® (Reference) | DYMISTA ® (Reference) |
|---|---|---|---|---|
| % Change from Baseline | — | 50.37 | 43.6 | 28.3 | 37.88 |

The results of the study show that a combination of mometasone furoate and olopatadine hydrochloride, when administered nasally to a human patient, provides an effective treatment of seasonal allergic rhinitis and clinically significant reduction in both nasal and non-nasal symptoms associated therewith. The magnitude of this relief for TNSS was clinically relevant (i.e., greater than 2 units in difference—which is generally considered as clinically relevant—between the Test Products and Placebo). Test Product-1 showed overall better symptom relief with a faster onset of action as compared to the Reference Products (PATANASE® and DYMISTA®).

Example 4

Phase II Clinical Study of Fixed Dose Combination of Mometasone and Olopatadine Nasal Spray in Human Patients The study is a double-blind, randomized, parallel-group, comparative study to evaluate the efficacy, safety and tolerability of two different strengths and regimens of a fixed dose combination of mometasone furoate and olopatadine hydrochloride nasal spray compared with a placebo nasal spray and individual monotherapy formulations of olopatadine hydrochloride nasal spray and mometasone furoate nasal spray, in subjects (12 years of age and older) with seasonal allergic rhinitis (SAR).

Key Objectives
  To compare the efficacy of mometasone furoate and olopatadine hydrochloride nasal spray once daily and mometasone furoate and olopatadine hydrochloride nasal spray twice daily with the placebo nasal spray and with the individual constituent monotherapies at the same dose in the same vehicle over 14 days of study treatment.
  To compare the onset of action between mometasone furoate and olopatadine hydrochloride nasal spray once daily and mometasone furoate and olopatadine hydrochloride nasal spray twice daily with the placebo and the individual constituent monotherapies at the same dose in the same vehicle, after the first dose of study drug administration.
  To assess the safety and tolerability of individual treatment arms.

TABLE E

| Investigational products and their administration | | |
|---|---|---|
| Code | Investigational product(s) | Administration |
| TP-1 | Olopatadine hydrochloride + mometasone furoate (665 µg + 25 µg) nasal spray | Twice daily (BID) in morning and evening |
| TP-2 | Olopatadine hydrochloride + mometasone furoate (665 µg + 50 µg) nasal spray | Once daily (QD) in morning |
| GO-1 | Olopatadine hydrochloride (665 µg) nasal spray | Once daily (QD) in morning |
| GO-2 | Olopatadine hydrochloride (665 µg) nasal spray | Twice daily (BID) in morning and evening |
| GM-1 | Mometasone furoate (50 µg) nasal spray | Once daily (QD) in morning |
| GM-2 | Mometasone furoate (25 µg) nasal spray | Twice daily (BID) in morning and evening |

Sample Size:
  A total of approximately 1,106 randomized subjects (158 subjects per treatment arm) will be enrolled in the study.
Key Subject Selection Criteria:
  1. Age ≥12 and older inclusive of either sex.
  2. Documented clinical history of SAR (for at least 2 years preceding the screening visit) with exacerbations (clinical evidence of active symptoms) and exhibiting a documented positive SPT (wheal diameter at least 5 mm greater than control wheal) to mountain cedar allergen.
  3. A 12-hour reflective TNSS≥8 out of a possible 12 and a congestion score of ≥2 for the AM assessment at the Screening Visit (Visit 1).
Study Design:
  Subjects will be randomized to treatment in a 1:1:1:1:1:1:1 ratio to the following seven treatment arms, at multiple study sites.
  The double-dummy design including two identical nasal spray bottles (one for morning [AM] dosing and one for evening [PM] dosing) are utilized for this study (Table F). The double-dummy design is ensured for adequate blinding considering that treatments being compared vary in dosing frequency (BID compared with QD).

TABLE F

Treatment Administration Using Two Identical Bottles of Nasal Sprays (2 sprays per nostril, total 4 sprays each bottle, per day)

| Code | Treatment Arm | Morning (AM) 1st bottle | Evening (PM) 2nd bottle |
|---|---|---|---|
| TP-1 | Olopatadine hydrochloride 665 µg + mometasone furoate 25 µg twice daily (BID) | Active | Active |
| TP-2 | Olopatadine hydrochloride 665 µg + mometasone furoate 50 µg once daily (QD) | Active | Placebo |
| GO-1 | Olopatadine hydrochloride nasal spray (665 µg) once daily (QD) | Active | Placebo |
| GO-2 | Olopatadine hydrochloride nasal spray (665 µg) twice daily (BID) | Active | Active |
| GM-1 | Mometasone furoate nasal spray (50 µg) once daily (QD) | Active | Placebo |
| GM-2 | Mometasone furoate nasal spray (25 µg) twice daily (BID) | Active | Active |
| Pbo | Placebo nasal spray | Placebo | Placebo |

This study consists of four visits to the study site. After the initial screening visit (Visit 1), subjects who meet all study selection criteria are required to undergo a single-blind placebo run-in period for 7-10 days. Following the completion of the run-in period, eligible subjects meeting the randomization criteria are enrolled and randomized to one of the seven treatment arms. Subjects are dispensed medication as per the randomization list. Randomized subjects are required to undergo a 2 week (14 days) treatment period as per the protocol to assess the efficacy and safety of the assigned treatment.

Key Evaluation Criteria (Clinical Endpoints):
Primary Endpoint
    Change from baseline in average AM and PM subject-reported 12-hour rTNSS (reflective TNSS) over the 14-day treatment period.
Secondary Endpoints
    Change from baseline in average AM and PM subject-reported 12-hour iTNSS (instantaneous TNSS) over the 14 day treatment period.
    Change from baseline in average AM and PM subject-reported 12-hour rTOSS (reflective TOSS) over the 14-day treatment period.
    Onset of action for each treatment are assessed by comparing the change from baseline in post-treatment iTNSS between each active treatment and placebo at defined time points (prior to first dose (pre-dose), 15 min, 30 min, 45 min, 60 min, 90 min, 120 min, 150 min, 180 min, 210 min, and 240 min) after the first study treatment for 4 hours.
    Change from baseline in the rhinoconjunctivitis quality of life questionnaire (RQLQ) on day 15 between treatment arms for subjects with impaired quality of life at baseline as defined by the RQLQ Score at the randomization visit (RV) of 3.0 or greater (RQLQ population).
Tertiary Efficacy Endpoints
Nasal symptoms:
    Change from baseline in AM subject-reported rTNSS over the 14-day treatment period.
    Change from baseline in AM subject-reported iTNSS over the 14-day treatment period.
    Change from baseline in PM subject-reported rTNSS over the 14-day treatment period.
    Change from baseline in PM subject-reported iTNSS over the 14-day treatment period.
    Change from baseline in subject-reported reflective individual nasal symptoms over the 14-day treatment period (AM, PM and average of AM and PM).
    Change from baseline in subject-reported instantaneous individual nasal symptoms over the 14-day treatment period (AM, PM and average of AM and PM).
    Change from baseline in average AM and PM subject-reported rTNSS and iTNSS for each day.
    Change from baseline in AM subject-reported rTNSS and iTNSS for each day.
    Change from baseline in PM subject-reported rTNSS and iTNSS for each day.
Ocular Symptoms:
    Change from baseline in average AM and PM subject-reported iTOSS (instantaneous TOSS) over the 14-day treatment period.
    Change from baseline in AM subject-reported rTOSS over the 14-day treatment period.
    Change from baseline in AM subject-reported iTOSS over the 14-day treatment period.
    Change from baseline in PM subject-reported rTOSS over the 14-day treatment period.
    Change from baseline in PM subject-reported iTOSS over the 14-day treatment period.
    Change from baseline in subject-reported reflective individual ocular symptoms over the 14-day treatment period (AM, PM and average AM and PM).
    Change from baseline in subject-reported instantaneous individual ocular symptoms over the 14-day treatment period (AM, PM and average AM and PM).
    Change from baseline in average of the AM and PM subject-reported rTOSS and iTOSS for each day.
    Change from baseline in AM subject-reported rTOSS and iTOSS for each day.
    Change from baseline in PM subject-reported rTOSS and iTOSS for each day.

The non-nasal symptoms are assessed in a similar manner to the ocular symptoms above.

Physician Assessed Nasal Symptom Score (PNSS) and Rhinoconjuntivitis Quality of Life Questionnaire (RQLQ):
    Physician assessed Nasal Symptom Score (PNSS) and physician assessed individual nasal symptoms at Day 15 (Visit 4).
    Individual domains of the RQLQ at Day 15 (Visit 4) for the RQLQ population (defined as subject with impaired Quality of Life at baseline).
    RQLQ at Day 15 (Visit 4) for the full analysis set (FAS).

Although the invention herein has been described with reference to particular embodiments, it is to be understood that these embodiments are merely illustrative of the principles and application of the present invention. It is therefore to be understood that numerous modifications may be made to the illustrative embodiments.

All publications, patents, and patent applications cited in this application are herein incorporated by reference to the same extent as if each individual publication, patent, or patent application was specifically and individually indicated to be incorporated herein by reference.

We claim:

1. A method of treating one or more symptoms associated with allergic rhinitis in a human subject in need thereof comprising twice daily nasal administration to the human subject of about 1330 mcg per nostril of olopatadine hydrochloride and about 50 mcg per nostril of mometasone furoate, wherein (i) the olopatadine hydrochloride and mometasone furoate are administered in a single pharmaceutical composition as a nasal spray, and (ii) the twice daily administration of the pharmaceutical composition provides a faster onset of action than twice daily administration of 1330 mcg per nostril of olopatadine hydrochloride alone.

2. The method according to claim 1, wherein each administration of the composition is two sprays of the composition in each nostril, and each spray comprises about 25 mcg mometasone furoate and about 665 mcg olopatadine hydrochloride.

3. The method according to claim 1, wherein the pharmaceutical composition is a suspension comprising mometasone furoate in particulate form and olopatadine in dissolved form.

4. The method according to claim 1, wherein the allergic rhinitis is perennial allergic rhinitis.

5. The method according to claim 1, wherein the allergic rhinitis is seasonal allergic rhinitis.

6. The method according to claim 1, wherein the human subject exhibits a positive skin prick test to an allergen.

7. A method of treating one or more symptoms of seasonal allergic rhinitis in a human in need thereof comprising twice daily nasal administration to the human subject of about 1330 mcg per nostril of olopatadine hydrochloride and about 50 mcg per nostril of mometasone furoate, wherein (i) the olopatadine hydrochloride and mometasone furoate are administered in a single pharmaceutical composition as a nasal spray, (ii) the twice daily administration of the pharmaceutical composition provides a faster onset of action than twice daily administration of 1330 mcg per nostril of olopatadine hydrochloride alone, and (iii) the pharmaceutical composition comprises mometasone furoate in particulate form and olopatadine hydrochloride in dissolved form.

8. The method according to claim 7, wherein the composition is administered twice daily for a period of 2 weeks.

9. The method according to claim 7, wherein each administration of the composition is two sprays of the composition in each nostril, and each spray comprises about 25 mcg of mometasone furoate and about 665 mcg of olopatadine hydrochloride.

10. The method according to claim 7, wherein the human subject exhibits a positive skin prick test to an allergen.

11. A method of reducing one or more symptoms associated with allergic rhinitis in a human subject in need thereof comprising twice daily nasal administration to the human subject of about 1330 mcg per nostril of olopatadine hydrochloride and about 50 mcg per nostril of mometasone furoate, wherein (i) the olopatadine hydrochloride and mometasone furoate are administered in a single pharmaceutical composition as a nasal spray, and (ii) the twice daily administration of the pharmaceutical composition provides a faster onset of action than twice daily administration of 1330 mcg per nostril of olopatadine hydrochloride alone.

12. The method according to claim 11, wherein each administration of the composition is two sprays of the composition in each nostril, and each spray comprises about 25 mcg mometasone furoate and about 665 mcg olopatadine hydrochloride.

13. The method according to claim 11, wherein the pharmaceutical composition is a suspension comprising mometasone furoate in particulate form and olopatadine in dissolved form.

14. The method according to claim 11, wherein the allergic rhinitis is perennial allergic rhinitis.

15. The method according to claim 11, wherein the allergic rhinitis is seasonal allergic rhinitis.

16. The method according to claim 11, wherein the human subject exhibits a positive skin prick test to an allergen.

17. The method according to claim 11, wherein the symptoms are selected from rhinorrhea, nasal congestion, nasal itching, sneezing, itching/burning eyes, tearing/watering eyes, redness of eyes, itching of ears or palate, coughing, ocular pruritus, excess lacrimation, headache, fatigue, malaise, and any combination of any of the foregoing.

18. A method of reducing eosinophil count in the nasal lavage of a human subject comprising twice daily nasal administration to the human subject of about 1330 mcg per nostril of olopatadine hydrochloride and about 50 mcg per nostril of mometasone furoate, wherein (i) the olopatadine hydrochloride and mometasone furoate are administered in a single pharmaceutical composition as a nasal spray, and (ii) the twice daily administration of the pharmaceutical composition provides a faster onset of action than twice daily administration of 1330 mcg per nostril of olopatadine hydrochloride alone.

19. A method of reducing total cell count in the nasal lavage of a human subject comprising twice daily nasal administration to the human subject of about 1330 mcg per nostril of olopatadine hydrochloride and about 50 mcg per nostril of mometasone furoate, wherein (i) the olopatadine hydrochloride and mometasone furoate are administered in a single pharmaceutical composition as a nasal spray, and (ii) the twice daily administration of the pharmaceutical composition provides a faster onset of action than twice daily administration of 1330 mcg per nostril of olopatadine hydrochloride alone.

20. The method of claim 1, wherein the symptoms are nasal symptoms.

21. The method of claim 7, wherein the symptoms are nasal symptoms.

22. The method of claim 11, wherein the symptoms are nasal symptoms.

23. The method of claim 18, wherein each administration of the composition is two sprays of the composition in each nostril, and each spray comprises about 25 mcg of mometasone furoate and about 665 mcg of olopatadine hydrochloride.

24. The method of claim 19, wherein each administration of the composition is two sprays of the composition in each nostril, and each spray comprises about 25 mcg of mometasone furoate and about 665 mcg of olopatadine hydrochloride.

25. The method of claim 1, wherein the subject is at least 12 years of age.

26. The method of claim 25, wherein the allergic rhinitis is perennial allergic rhinitis.

27. The method of claim 25, wherein the allergic rhinitis is seasonal allergic rhinitis.

28. The method of claim 27, wherein each administration of the composition is two sprays of the composition in each nostril, and each spray comprises about 25 mcg of mometasone furoate and about 665 mcg of olopatadine hydrochloride.

29. The method of claim 11, wherein the subject is at least 12 years of age.

30. The method of claim 29, wherein the allergic rhinitis is perennial allergic rhinitis.

31. The method of claim 29, wherein the allergic rhinitis is seasonal allergic rhinitis.

32. The method of claim 31, wherein each administration of the composition is two sprays of the composition in each nostril, and each spray comprises about 25 mcg of mometasone furoate and about 665 mcg of olopatadine hydrochloride.

* * * * *